US011345940B2

(12) United States Patent
Kim et al.

(10) Patent No.: US 11,345,940 B2
(45) Date of Patent: May 31, 2022

(54) **MICROORGANISM OF GENUS *CORYNEBACTERIUM* PRODUCING L-ARGININE AND METHOD FOR PRODUCING L-ARGININE USING THE SAME**

(71) Applicant: CJ Cheiljedang Corporation, Seoul (KR)

(72) Inventors: Seon Hye Kim, Gyeonggi-do (KR); Hyung Joon Kim, Seoul (KR); Haena Oh, Gyeonggi-do (KR); Byoung Hoon Yoon, Seoul (KR); Min Gyeong Kang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/461,490

(22) PCT Filed: Dec. 18, 2018

(86) PCT No.: PCT/KR2018/016115
§ 371 (c)(1),
(2) Date: May 16, 2019

(87) PCT Pub. No.: WO2019/124932
PCT Pub. Date: Jun. 27, 2019

(65) Prior Publication Data
US 2021/0139937 A1    May 13, 2021

(30) Foreign Application Priority Data

Dec. 19, 2017  (KR) ..................... 10-2017-0175046

(51) Int. Cl.
| *C12P 13/10* | (2006.01) |
| *C07K 14/34* | (2006.01) |
| *C12N 1/20*  | (2006.01) |
| *C12N 15/77* | (2006.01) |

(52) U.S. Cl.
CPC .............. *C12P 13/10* (2013.01); *C07K 14/34* (2013.01); *C12N 1/20* (2013.01); *C12N 15/77* (2013.01)

(58) Field of Classification Search
None
See application file for complete search history.

(56) References Cited

U.S. PATENT DOCUMENTS

| 3,878,044    | A    | 4/1975  | Kubota et al. |
| 8,034,602    | B2   | 10/2011 | Park et al. |
| 8,993,272    | B2   | 3/2015  | Kim et al. |
| 10,870,871   | B2 * | 12/2020 | Kim .............. C12N 15/77 |
| 2002/0045223 | A1   | 4/2002  | Suga et al. |
| 2017/0226545 | A1   | 8/2017  | Bae et al. |

FOREIGN PATENT DOCUMENTS

| EP | 1108790    | A2 | 6/2001  |
| KR | 100791659  | B1 | 1/2008  |
| KR | 100924065  | B1 | 10/2009 |
| KR | 101102263  | B1 | 1/2012  |
| WO | 2007037503 | A1 | 4/2007  |
| WO | 2015165740 | A2 | 11/2015 |

OTHER PUBLICATIONS

M.E. Van Der Rest er al., A heat shock following electroporation induces highly efficient transformation of Corynebacterium glutamicum with xenogeneic plasmid DNA, Appl. Microbiol. Biotechnol. (1999) 52:541-545, 5 pages.
Lipman and Pearson, Rapid and Sensitive Sequence Comparison with FASTP and FASTA, Methods in Enzymology, vol. 183, p. 63-98, Copyright 1990, 36 pages.
International Search Report, Corynebacterium sp. Microorganism Producing L-Arginine and L-Arginine Production Method Using Same, WO2019/124932A3, Jun. 27, 2019, CJ Cheiljedang Corpration, mailing date of ISR May 23, 2019, 5 pages including English Translation.
Karlin and Altschul, Applications and statistics for multiple high-scoring segments in molecular sequences Pro. Natl. Acad. Sci. USA, 90, pp. 5873-5877, Jun. 1993, 5 pages.
Gerhardt et a, Manual of Methods for General Bacteriology by the American Society for Bacteriology, Washington D.C., USA, 1981, 1 page.
Moore S., Stein W. H., Photometric ninhydrin method for use in the chromatography of amino acids. J. Biol. Chem. Jun. 8, 1948, 176, 367-388, 23 pages.
Nishio, Y., et al., Corynebacterium glutamicum DNA, complete genome, strain: AJ1511, GenBank: APO17557.2, Jun. 17, 2017, National Center for Biotechnology Information, U.S. National Library of Medicine, Bethesda, Maryland, 2 pages.
Nishio, Y., et al., UPF0272 protein cgR_2381 [Corynebacterium glutamicum], GenBank: BAV24083.1, Jun. 17, 2017, National Center for Biotechnology Information, U.S. National Library of Medicine, Bethesda, Maryland, 575 pages.
Seok Hyun Park et al., Metabolic engineering of Corynebacterium glutamicum for L-arginine production, Nature Communications, Aug. 5, 2014, pp. 1-9, vol. 5, Macmillan Publishers Limited, London, United Kingdom, 9 pages.
Vehary Sakanyan et al., Genes and enzymes of the acetyl cycle of arginine biosynthesis in Corynebacterium glutamicum: enzyme evolution in the early steps of the arginine pathway, Microbiology, 142:9-108, 1996, 10 pages.
Ghochikyan et al, Arginine Operator Binding by Heterologous and Chimeric ArgR Repressors from *Escherichia coli* and Bacillus stearothermophilus, J Bacteriol. Dec. 2002; vol. 184 No. 23, pp. 6602-6614, 13 pages.
Office Action dated Dec. 7, 2021 for Indian Appn. No. 201937026262, 7 pgs.

* cited by examiner

*Primary Examiner* — Hope A Robinson
(74) *Attorney, Agent, or Firm* — Brooks Kushman P.C.

(57) ABSTRACT

A microorganism of the genus *Corynebacterium* producing L-arginine, and a method for producing L-arginine using the same.

6 Claims, No Drawings
Specification includes a Sequence Listing.

MICROORGANISM OF GENUS *CORYNEBACTERIUM* PRODUCING L-ARGININE AND METHOD FOR PRODUCING L-ARGININE USING THE SAME

CROSS-REFERENCE TO RELATED APPLICATION

This application is the U.S. national phase of PCT Application No. PCT/KR2018/016115 filed on Dec. 18, 2018, which claims priority to KR Patent Application No. 10-2017-0175046 filed on Dec. 19, 2017, the disclosures of which are incorporated in their entirety by reference herein.

SEQUENCE LISTING

The text file OPA18459-SequenceListing of size 6.35 KB created Sep. 23, 2020, filed herewith, is hereby incorporated by reference.

TECHNICAL FIELD

The present disclosure relates to a microorganism of the genus *Corynebacterium* producing L-arginine, and a method for producing L-arginine using the same.

BACKGROUND ART

L-Arginine is contained in its free form in plant seeds or garlic, and in addition to being used in amino acid fortified dietary supplements, it is widely used in medicaments, foods, and the like. Examples of the medicinal applications of L-arginine include liver function enhancers, brain function enhancers, therapeutics for male infertility, and general amino acid formulations. Representative among the foods to which L-arginine is applied are fish paste additives, health beverage additives, and salt substitutes for patients with hypertension. Therefore, L-arginine is a material that has recently attracted much attention.

Microorganisms of the genus *Corynebacterium*, in particular *Corynebacterium glutamicum*, are gram-positive microorganisms widely used in the production of L-amino acids. For the production of L-arginine, target material-specific approaches, such as a method of increasing the expression of a gene encoding an enzyme mainly involved in L-arginine synthesis in a strain of *Corynebacterium*, or a method of deleting a gene unnecessary for the L-arginine biosynthesis, are mainly used (Korean Patent No. 10-1102263). However, there is still a growing need for research on methods that can efficiently produce L-arginine with high yield.

Under such circumstances, the present inventors have made intensive efforts to develop a microorganism capable of producing L-arginine with high efficiency, and as a result, they have completed the present disclosure by confirming that the production yield of L-arginine is increased in a microorganism of the genus *Corynebacterium* in which a gene encoding a protein, the function of which is unknown, is deleted.

DISCLOSURE

Technical Problem

An object of the present disclosure is to provide a microorganism of the genus *Corynebacterium* producing L-arginine, wherein a protein including an amino acid sequence of SEQ ID NO: 1 is inactivated.

Another object of the present disclosure is to provide a method for producing L-arginine by using the microorganism.

Technical Solution

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the above objects, an aspect of the present disclosure provides a microorganism of the genus *Corynebacterium* producing L-arginine, wherein a protein including an amino acid sequence of SEQ ID NO: 1 is inactivated.

As used herein, the term "L-arginine" refers to an L-amino acid having the chemical formula of $C_6H_{14}N_4O_2$, and is a conditionally essential amino acid present in all organisms. L-Arginine is known to be mainly produced by microorganisms of the genus *Corynebacterium*, but it is known that these are subject to feedback inhibition by intracellular arginine (Vehary Sakanyan, et al., Microbiology, 142:9-108, 1996). Therefore, these microorganisms are known to have a limit in producing L-arginine with high yield. The present inventors surprisingly found that the production of L-arginine was increased when a protein including an amino acid sequence of SEQ ID NO: 1, the function of which is unknown, was inactivated, thereby providing a novel microorganism for producing L-arginine.

As used herein, the term "protein including an amino acid sequence of SEQ ID NO: 1" refers to a protein that is inherently present in a microorganism of the genus *Corynebacterium* or a hypothetical protein whose function is not known. For example, the protein including an amino acid sequence of SEQ ID NO: 1 may be a protein (essentially) consisting of the amino acid sequence of SEQ ID NO: 1, but is not limited thereto.

Additionally, although described as "a protein consisting of a particular SEQ ID NO" in the present disclosure, such expression does not exclude a mutation in the protein that can occur by a meaningless sequence addition upstream or downstream of the amino acid sequence of the corresponding SEQ ID NO, or a naturally occurring mutation therein, or a silent mutation therein, as long as the protein having such mutation has an activity the same as or corresponding to that of the protein which consists of an amino acid sequence of the corresponding SEQ ID NO. Even when the sequence addition or mutation is present, it obviously belongs to the scope of the present disclosure.

In one exemplary embodiment, the protein including an amino acid sequence of SEQ ID NO: 1 may include an amino acid sequence having a homology to SEQ ID NO: 1 of at least 80%. The protein including an amino acid sequence having a homology to SEQ ID NO: 1 of at least 80% may include a protein including an amino acid sequence having a homology to the amino acid sequence of SEQ ID NO: 1 of at least 80%, specifically at least 83%, at least 84%, at least 88%, at least 90%, at least 93%, at least 95%, or at least 97%. It is apparent that a protein having an amino acid sequence in which the sequence is partially deleted, modified, substituted, or inserted is included in the scope of the present disclosure, as long as a sequence having a homology to the sequence shows biological activity practically equivalent or corresponding to an amino acid sequence of SEQ ID NO: 1.

Additionally, the protein including an amino acid sequence of SEQ ID NO: 1 may be encoded by a gene including the polynucleotide sequence of SEQ ID NO: 2. In addition, the protein may be encoded by a gene consisting or essentially consisting of the polynucleotide sequence of SEQ ID NO: 2, but is not limited thereto.

Additionally, the protein of the present disclosure may be encoded not only by a gene including the polynucleotide sequence of SEQ ID NO: 2, but also by a gene including a polynucleotide having a homology to SEQ ID NO: 2 of at least 80%.

Specifically, a polynucleotide sequence capable of encoding a protein including an amino acid sequence having a homology to SEQ ID NO: 1 above of at least 80% can be included within the scope of the present disclosure, but the protein may be encoded by a gene including a polynucleotide sequence having a homology to the above polynucleotide sequence of SEQ ID NO: 2 of at least 80%, specifically at least 83%, at least 84%, at least 88%, at least 90%, at least 93%, at least 95%, or at least 97%. In addition, based on genetic code degeneracy, variants of the sequences encoding the same amino acid sequence also can be included within the scope of the present disclosure.

As used herein, the term "homology" refers to identity with a given amino acid sequence or nucleotide sequence, and the homology may be expressed as a percentage. In the present disclosure, a homology sequence having identical or similar activity to the given amino acid sequence or polynucleotide sequence is expressed as "% homology".

The homology to the amino acid sequence or nucleotide sequence can be determined, for example, by using the algorithm BLAST (see Karlin and Altschul, Pro. Natl. Acad. Sci. USA, 90, 5873(1993)) or FASTA (see Pearson, Methods Enzymol., 183, 63, 1990)). Based on the algorithm BLAST, a program called BLASTN or BLASTX has been developed (see http://www.ncbi.nlm.nih.gov).

As used herein, the term "inactivation" means that the protein is not expressed at all, or the protein is expressed but exhibits no activity or a reduction in the activity, as compared with that of a parent strain, native strain, or a strain before modification. The reduction refers to a concept including a case where the activity of a protein is reduced compared to that of a protein originally possessed in a microorganism due to modification, deletion, etc. of the gene encoding the protein, a case where the level of overall protein activity in cells is lower than that of the native strain or that of the strain before modification due to inhibition of expression or inhibition of translation of the gene encoding the same, or a combination thereof.

In the present disclosure, it was identified for the first time that the inactivation of the protein is related to the productivity of L-arginine.

In the present disclosure, the inactivation may be accomplished by various methods well known in the art. Examples of the methods may include 1) a method of deleting the entirety or part of the gene encoding the protein; 2) a method of modifying an expression control sequence so that expression of the gene encoding the protein is reduced; 3) a method of modifying the sequence of the gene encoding the protein so that the activity of the protein is removed or attenuated; 4) a method of introducing an antisense oligonucleotide (e.g., antisense RNA) which complementarily binds to a transcript of the gene encoding the protein; 5) a method of making the attachment of a ribosome impossible by forming a secondary structure by adding a Shine-Dalgarno sequence and its complementary sequence on the front end of the Shine-Dalgarno sequence of the gene encoding the protein; 6) a method of reverse transcription engineering (RTE), which adds a promoter to be reversely transcribed on the 3' terminus of the open reading frame (ORF) of the polynucleotide sequence of the gene encoding the protein, etc., and may also include a combination thereof, but are not particularly limited thereto.

Specifically, the method of modifying the expression control sequence may be achieved by applying a variety of methods well known in the art. For example, the method may be carried out by inducing a modification of the expression control sequence in the polynucleotide sequence via deletion, insertion, non-conservative or conservative substitution, or a combination thereof to further attenuate the activity of the expression control sequence, or by substituting the expression control sequence with a polynucleotide sequence having a weaker activity. The expression control sequence may include a promoter, an operator sequence, a sequence encoding a ribosome-binding region, and sequences controlling the termination of transcription and translation, but is not limited thereto.

Furthermore, the method of modifying the nucleotide sequence may be carried out by inducing a modification in the sequence via deletion, insertion, non-conservative or conservative substitution, or a combination thereof in the nucleotide sequence to further attenuate the enzyme activity; or by substituting the nucleotide sequence with a nucleotide sequence which was improved to have weaker activity or a nucleotide sequence which was improved to have no activity, but is not limited thereto.

Additionally, the method of deleting part or the entirety of the gene encoding the protein may be performed by substituting a polynucleotide encoding an endogenous target protein within the chromosome with a polynucleotide or a marker gene where part of the nucleotide sequence is deleted, via a vector for chromosomal insertion into the microorganism. In an exemplary embodiment of the method of deleting part or the entirety of the polynucleotide, a method of deleting the polynucleotide by homologous recombination may be used, but is not limited thereto.

Additionally, the method of deleting part or the entirety of the gene may be carried out by inducing a mutation using light such as UV, or chemicals, and by selecting a strain having the deleted target gene from the obtained mutants. The method of deleting the gene may include a method of using a genetic recombination technique. For example, a nucleotide sequence or a vector including a nucleotide sequence having homology with a target gene is introduced into the microorganism to cause homologous recombination. Further, the nucleotide sequence or vector to be introduced may include a dominant selection marker.

As used herein, the term "microorganism producing L-arginine" or "microorganism having L-arginine productivity" refers to a microorganism naturally having an ability to produce L-arginine or a microorganism which is prepared by imparting an ability to produce L-arginine to a parent strain having no ability to produce L-arginine. For example, the ability to produce L-arginine may be imparted by inactivating the activity of the protein including an amino acid sequence of SEQ ID NO: 1 and/or by enhancing expression of the gene encoding enzymes biosynthesizing L-arginine.

Herein, examples of the enzymes biosynthesizing L-arginine include N-acetylglutamyl phosphate reductase (ArgC), ornithine acetyltransferase (ArgJ), N-acetylglutamate kinase (ArgB), acetylornithine transaminase (ArgD), ornithine carbamoyltransferase (ArgF), argininosuccinic acid synthetase (ArgG), argininosuccinic acid lyase (argH), and carbamoyl phosphate synthetase. These enzymes are placed in the Arg operon (argCJBDFRGH) and are regulated by an arginine repressor encoded by argR (J Bacteriol. 2002 December; 184(23):6602-14.). Therefore, an ability to produce L-arginine may be imparted by attenuating the arginine repressor (US2002-0045223) or overexpressing at least one of the biosynthesis genes.

In the present disclosure, the microorganism producing L-arginine is a microorganism in which a protein including an amino acid sequence of SEQ ID NO: 1 is inactivated. In addition, for the purpose of the present disclosure, the microorganism may be any microorganism capable of producing L-arginine by inactivating the protein including the amino acid sequence of SEQ ID NO: 1. As a specific example, the microorganism may include a microorganism strain such as a microorganism of the genus *Escherichia*, a microorganism of the genus *Serratia*, a microorganism of the genus *Erwinia*, a microorganism of the genus *Enterobacteria*, a microorganism of the genus *Salmonella*, a microorganism of the genus *Streptomyces*, a microorganism of the genus *Pseudomonas*, a microorganism of the genus *Brevibacterium*, or a microorganism of the genus *Corynebacterium*, and specifically may be a microorganism of the genus *Corynebacterium*. For the purpose of the present disclosure, the microorganism may be a microorganism of the genus *Corynebacterium* producing L-arginine.

The "microorganism of the genus *Corynebacterium* producing L-arginine" refers to a microorganism of the genus *Corynebacterium* which has an L-arginine-producing ability naturally or due to modification. It is already known that the microorganism of the genus *Corynebacterium* can produce L-arginine. However, its L-arginine-producing ability is remarkably low, and genes or mechanisms involved in the production have not yet been revealed. Therefore, in the present disclosure, the microorganism of the genus *Corynebacterium* producing L-arginine refers to a native microorganism itself or a microorganism of the genus *Corynebacterium* in which the activity of a foreign gene involved in the L-arginine production mechanism is reinforced or inactivated so as to have an improved L-arginine-producing ability.

In the present disclosure, the "microorganism of the genus *Corynebacterium*" may include all microorganisms of the genus *Corynebacterium*. Specifically, the microorganism may be *Corynebacterium glutamicum*, *Corynebacterium ammoniagenes*, *Corynebacterium thermoaminogenes*, *Brevibacterium flavum*, *Corynebacterium efficiens*, *Corynebacterium marls*, *Corynebacterium lubricantis*, *Corynebacterium doosanense*, *Corynebacterium pilosum*, *Corynebacterium cystitidis*, *Corynebacterium uterequi*, *Corynebacterium renale*, or *Brevibacterium lactofermentum*, and more specifically may be *Corynebacterium glutamicum*.

The present disclosure provides a method for producing L-arginine, comprising: culturing the microorganism according to the present disclosure in a medium.

The microorganism according to the present disclosure is as described above.

In the method of the present disclosure, the culturing of the microorganism of the genus *Corynebacterium* may be carried out using any culture condition and culturing method known in the art.

As used herein, the term "culturing" means that microorganisms are grown in appropriately artificially controlled environmental conditions. In the present disclosure, the method of culturing the microorganism of the genus *Corynebacterium* producing L-arginine may be carried out using a method widely known in the art. Specifically, a batch process or a continuous process such as a fed-batch process or a repeated fed-batch process may be used for the culturing, but the culturing is not limited thereto.

For use in the culturing, a medium must satisfy the requirement of the strain employed. Culture media suitable for use in culturing Corynebacteria strains are well known in the art (e.g., Manual of Methods for General Bacteriology by the American Society for Bacteriology, Washington D.C., USA, 1981).

Sugar sources that may be used in the medium include sugars and carbohydrates such as glucose, saccharose, lactose, fructose, maltose, starch, or cellulose; oils and fats such as soybean oil, sunflower oil, castor oil, or coconut oil; fatty acids such as palmitic acid, stearic acid, or linoleic acid; alcohols such as glycerol or ethanol; and organic acids such as acetic acid. These substances may be used individually or in a mixture, but are not limited thereto.

Nitrogen sources which may be used include compounds containing organic nitrogen, such as peptone, yeast extract, meat extract, malt extract, corn steep liquor, soybean meal, and urea, or inorganic compounds such as ammonium sulfate, ammonium chloride, ammonium phosphate, ammonium carbonate, and ammonium nitrate. The nitrogen sources may also be used individually or as a mixture, but are not limited thereto.

Phosphorus sources which may be used include potassium dihydrogen phosphate or dipotassium hydrogen phosphate or the corresponding sodium salts. The culture medium may furthermore contain metal salts such as magnesium sulfate or iron sulfate, which are required for growth. Finally, essential growth substances such as amino acids and vitamins may be used in addition to the above-mentioned substances. Moreover, suitable precursors may be added to the culture medium. Said substances may be added to the culture in a batch or a continuous manner by a suitable method during culturing.

The pH of the culture product may be controlled by using basic compounds such as sodium hydroxide, potassium hydroxide, ammonia, or aqueous ammonia; or acidic compounds such as phosphoric acid or sulfuric acid in a suitable manner. Foaming can be controlled by using antifoaming agents such as fatty acid polyglycol esters. Aerobic conditions can be maintained by introducing oxygen or oxygen containing gas mixtures (e.g., air) into the culture. The culture temperature may be usually from 20° C. to 45° C., specifically from 25° C. to 40° C. Culturing may be continued until a desired amount of L-amino acids has been produced. Specifically, the culturing time may be 10 hours to 160 hours.

In the method of the present disclosure, the culturing may be performed continuously or in a batch process or in a fed-batch or repeated fed-batch process. This culturing may be performed using any method well known in the art.

The separation of L-arginine from a culture product may be carried out by a conventional method known in the art. For the separation method above, methods such as centrifugation, filtration, ion exchange chromatography, crystallization, etc. may be used. For example, a supernatant, obtained by centrifuging the culture product at a low speed and removing biomass, may be separated by ion exchange chromatography, but the method is not limited thereto.

In the method of the present disclosure, recovering L-arginine from the microorganism or the medium may be further included after the culturing.

The recovering may include a purification process.

Advantageous Effects

The microorganism of the present disclosure, which produces L-arginine, can produce L-arginine with high efficiency. Additionally, the produced L-arginine can be applied not only to animal feeds or animal feed additives, but also to various products such as human food or food additives, medicines, etc.

DETAILED DESCRIPTION OF THE INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Construction of Random Mutant Library Using Transposon

To obtain a strain having increased L-arginine productivity, a vector library was constructed in the following manner.

First, using *Corynebacterium glutamicum* KCCM10741P (Korean Patent No. 0791659) as a parent strain, a plasmid obtained using the EZ-Tn5™ <R6Kγori/KAN-2>Tnp Transposome™ Kit (Epicentre) was transformed into the parent strain by an electric pulse method (Appl. Microbiol. Biotechnol. (1999) 52:541-545). Then, the strain was spread on a complex medium plate containing kanamycin (25 mg/L), and thereby about 20,000 colonies were obtained.

<Complex Medium Plate (pH 7.0)>

10 g glucose, 10 g peptone, 5 g beef extract, 5 g yeast extract, 18.5 g brain heart infusion, 2.5 g NaCl, 2 g urea, 91 g sorbitol, 20 g agar (per liter of distilled water)

Example 2: Random Mutant Library Screening Using Transposon

Each of about 20,000 colonies obtained in Example 1 was inoculated onto 300 μL of the following selective medium and cultured in a 96-deep-well plate at 30° C. at 1,000 rpm for about 24 hours.

<Selective Medium (pH 8.0)>

10 g glucose, 5.5 g ammonium sulfate, 1.2 g MgSO$_4$7H$_2$O, 0.8 g KH$_2$PO$_4$, 16.4 g K$_2$HPO$_4$, 100 μg biotin, 1 mg thiamine HCl, 2 mg calcium-pantothenate, 2 mg nicotinamide (per liter of distilled water)

To analyze the amount of L-arginine produced in the culture, the ninhydrin method was used (Moore, S., Stein, W. H., Photometric ninhydrin method for use in the chromatography of amino acids. J. Biol. Chem. 1948, 176, 367-388).

After completion of the culturing, 10 μL of the culture supernatant was reacted with 190 μL of a ninhydrin reaction solution at 65° C. for 30 minutes, and then the absorbance at a wavelength of 570 nm was measured with a spectrophotometer. Based on the results of the measurement, about 60 colonies showing higher absorbance than the *Corynebacterium glutamicum* KCCM10741P strain used as the control were selected as mutant strains. It was confirmed that other colonies showed absorbance similar to or lower than that of the *Corynebacterium glutamicum* KCCM10741P strain used as the control.

About 60 strains selected as described above were cultured again in the same manner as described above, and then subjected to the ninhydrin reaction. As a result, the top ten mutant strains having increased L-arginine productivity compared to the *Corynebacterium glutamicum* KCCM10741P strain used as the parent strain were selected.

Example 3: Analysis of L-Arginine Productivity of Selected Random Mutant Strains In order to finally select strains whose L-arginine productivity was reproducibly increased from the ten mutants selected in Example 2, flask culture was performed using the following medium. After completing of the culturing, the concentration of L-arginine in the culture was analyzed by HPLC. The concentration of L-arginine produced by each of the mutant strains is shown in Table 1 below.

<Production Medium (pH 7.0)>

6% glucose, 3% ammonium sulfate, 0.1% monopotassium phosphate, 0.2% magnesium sulfate heptahydrate, 1.5% corn steep liquor (CSL), 1% NaCl, 0.5% yeast extract, 100 mg/L biotin, 3% CaCO$_3$, (per liter of distilled water)

TABLE 1

Concentrations of L-arginine produced by 10 selected random mutant strains

| | Strains | L-Arginine (g/L) | | | |
|---|---|---|---|---|---|
| | | Batch 1 | Batch 2 | Batch 3 | Average |
| Control | KCCM10741P | 3 | 3.1 | 3.1 | 3.07 |
| 1 | KCCM10741P/mt-1 | 2.8 | 3 | 2.7 | 2.83 |
| 2 | KCCM10741P/mt-2 | 3.1 | 3 | 3.2 | 3.10 |
| 3 | KCCM10741P/mt-3 | 3.3 | 3.2 | 3.4 | 3.30 |
| 4 | KCCM10741P/mt-4 | 2.5 | 2.2 | 2.1 | 2.27 |
| 5 | KCCM10741P/mt-5 | 2.9 | 3 | 3.2 | 3.03 |
| 6 | KCCM10741P/mt-6 | 3.5 | 3.2 | 3.2 | 3.30 |
| 7 | KCCM10741P/mt-7 | 3.2 | 3.3 | 3.3 | 3.27 |
| 8 | KCCM10741P/mt-8 | 3.4 | 3 | 3.2 | 3.20 |
| 9 | KCCM10741P/mt-9 | 2.7 | 2.7 | 3 | 2.80 |
| 10 | KCCM10741P/mt-10 | 3.6 | 3.9 | 3.5 | 3.67 |

Among the 10 selected mutant strains, KCCM10741P/mt-10 was finally selected as a strain whose L-arginine productivity was significantly increased.

Example 4: Identification of Causes of Increased L-Arginine Productivity of Finally Selected Strain In this Example, an experiment was performed on the mutant strain finally selected in Example 3 in order to identify genes deleted by random insertion of the transposon.

Genomic DNA was extracted from KCCM10741P/mt-10, digested, and then ligated, and the ligation product was transformed into *E. coli* DH5α. The transformed *E. coli* cells were plated on an LB solid medium containing kanamycin (25 mg/L). Twenty transformed colonies were selected, and then plasmids containing an unknown gene portion were obtained. The nucleotide sequences were analyzed using primer 1 (SEQ ID NO: 3) and primer 2 (SEQ ID NO: 4) of the EZ-Tn5™ <R6Kγori/KAN-2>Tnp Transposome™ Kit. As a result, it was confirmed that the deleted and inactivated gene had the nucleotide sequence of SEQ ID NO: 2 encoding the amino acid sequence of SEQ ID NO: 1

Primer 1 (SEQ ID NO: 3):
ACCTACAACAAAGCTCTCATCAACC

Primer 2 (SEQ ID NO: 4):
CTACCCTGTGGAACACCTACATCT

Accordingly, in order to confirm whether the protein including the amino acid sequence of SEQ ID NO: 1 has an effect on the ability to produce L-arginine upon inactivation of the protein, the gene above was selected as a candidate gene for deletion.

Example 5: Construction of Recombinant Vector for Deletion of the Gene Comprising the Nucleotide Sequence of SEQ ID NO: 2

In this Example, in order to confirm the influence of the inactivation of the gene comprising the nucleotide sequence of SEQ ID NO: 2 and that of the production of L-arginine, a recombinant plasmid for deleting the gene, selected in Example 4, on the chromosome of the *Corynebacterium* L-arginine-producing strain was constructed.

First, primers 3 to 6 shown in Table 2 were synthesized in order to prepare a recombinant vector capable of deleting the gene on the chromosome of the microorganism of the genus *Corynebacterium*.

TABLE 2

| Primers used | Nucleotide sequences |
| --- | --- |
| Primer 3 (SEQ ID NO: 5) | CCGCTCGAGACATCGAAATCGTA AGGGTA |
| Primer 4 (SEQ ID NO: 6) | CAGCATTGACAAGCAGTTCT |
| Primer 5 (SEQ ID NO: 7) | AGAACTGCTTGTCAATGCTGGGC CCTTTCCCAGGTGGCAT |
| Primer 6 (SEQ ID NO: 8) | CCGCTCGAGAAGGCCACCGCTGC AGACCG |

Specifically, in order to delete the ORF region (SEQ ID NO: 2) of the gene, primer 3 (SEQ ID NO: 5), primer 4 (SEQ ID NO: 6), primer 5 (SEQ ID NO: 7), and primer 6 (SEQ ID NO: 8) were synthesized so that an XhoI restriction enzyme site is present at both the 5' terminus and the 3' terminus. PCR was carried out with the chromosomal DNA of *Corynebacterium glutamicum* KCCM10741P as a template using primers 3 to 6 above. As a result, it was confirmed that each of the DNA fragments corresponding to the front and rear portions of the part where the protein encoded by the gene is encoded was amplified by 500 bp, respectively. Herein, after denaturation at 95° C. for 5 minutes, PCR was carried out for a total of 30 cycles under the following conditions: denaturation at 94° C. for 30 seconds, annealing at 56° C. for 30 seconds, and polymerization at 72° C. for 1 minute. Thereafter, the polymerization reaction was carried out at 72° C. for 7 minutes. Next, a pDZ vector (Korean Patent No. 10-0924065), which is not replicable in *Corynebacterium glutamicum*, was treated with an XhoI restriction enzyme, and then the obtained PCR product was fusion-cloned. The fusion cloning was carried out using an In-Fusion® HD Cloning Kit (Clontech). Thereafter, the resultant was trans- formed into *E. coli* DH5α, and then plated on an LB solid medium containing kanamycin (25 mg/L).

A colony transformed with a plasmid having the desired gene inserted therein was selected by PCR, and then the plasmid was isolated using a plasmid extraction technique. The plasmid was named "pDZ-ΔRS1".

Example 6: Construction of *Corynebacterium glutamicum* KCCM10741P with the Deletion of the Gene Comprising the Nucleotide Sequence of SEQ ID NO: 2, and Evaluation of L-Arginine Productivity of the Constructed Strain Based on the L-arginine-producing strain of the genus *Corynebacterium*, which is the KCCM10741P strain, a strain in which the gene comprising the nucleotide sequence of SEQ ID NO: 2 is deleted was constructed, and the L-arginine productivity of the constructed strain was evaluated.

Specifically, the recombinant plasmid pDZ-ΔRS1 prepared in Example 5 was transformed into *Corynebacterium glutamicum* KCCM10741P, which is an L-arginine-producing strain, by homologous recombination on the chromosome (van der Rest et al., Appl Microbiol Biotechnol 52:541-545, 1999).

Next, the transformant was grown on a solid medium plate containing 4% sucrose to allow a second recombination to take place. After completion of the second recombination, deletion of the gene on the chromosome of the transformed *Corynebacterium glutamicum* strain was confirmed by PCR using primer 3 and primer 6. The recombinant strain was named "*Corynebacterium glutamicum* KCCM10741P-RS1".

In order to analyze the L-arginine productivity, the constructed *Corynebacterium glutamicum* KCCM10741P-RS1 strain and the parent strain *Corynebacterium glutamicum* KCCM10741P were cultured in the following manner.

Each of the parent strain *Corynebacterium glutamicum* KCCM10741P and the *Corynebacterium glutamicum* KCCM10741P-RS1 strain constructed in Example 6 was inoculated into a 250 mL corner-baffled flask containing 25 mL of the following seed medium and shake-cultured at 200 rpm at 30° C. for 20 hours. Next, 1 mL of each of the seed cultures was inoculated into a 250 mL corner-baffle flask containing 24 mL of the following production medium and shake-cultured at 200 rpm at 30° C. for 72 hours. The composition of the seed medium and the composition of the production medium were as follows.

<Seed Medium (pH 7.0)>

20 g glucose, 10 g peptone, 5 g yeast extract, 1.5 g urea, 4 g $KH_2PO_4$, 8 g $K_2HPO_4$, 0.5 g $MgSO_4 \cdot 7H_2O$, 100 µg biotin, 1 mg thiamine HCl, 2 mg calcium pantothenate, 2 mg nicotinamide (per liter of distilled water)

<Production Medium (pH 7.0)>

6% glucose, 3% ammonium sulfate, 0.1% monopotassium phosphate, 0.2% magnesium sulfate heptahydrate, 1.5% corn steep liquor (CSL), 1% NaCl, 0.5% yeast extract, 100 mg/L biotin (per liter of distilled water)

After completion of the culturing, the amount of L-arginine produced was measured by HPLC, and the concentration of L-arginine analyzed is shown in Table 3 below.

TABLE 3

Analysis of L-arginine productivity of *Corynebacterium glutamicum* KCCM10741P in which the gene comprising the nucleotide sequence of SEQ ID NO: 2 is deleted

| Strains | L-Arginine (g/L) | | | |
|---|---|---|---|---|
| | Batch 1 | Batch 2 | Batch 3 | Average |
| KCCM10741P | 3.0 | 3.1 | 3.1 | 3.06 |
| KCCM10741P-RS1 | 3.8 | 3.9 | 3.8 | 3.83 |

Based on the results above, it was confirmed that KCCM10741P-RS1, in which the gene is deleted from *Corynebacterium glutamicum* KCCM10741P (i.e., the L-arginine-producing strain), had the L-arginine productivity which is increased by 25% on average compared to the parent strain.

The KCCM10741P-RS1 strain was named "CA06-2830", and was deposited to the Korean Culture Center of Microorganisms (KCCM), which is an international depositary authority under the Budapest Treaty, on Dec. 15, 2017, and assigned Accession No. KCCM12187P.

Therefore, it was confirmed that the L-arginine productivity could be improved by deleting the gene comprising the nucleotide sequence of SEQ ID NO: 2 from the microorganism of the genus *Corynebacterium*.

Example 7: Construction of Recombinant Vector for Attenuating the Gene

Comprising the Nucleotide Sequence of SEQ ID NO: 2

In order to construct a recombinant vector capable of attenuating the gene comprising the nucleotide sequence of SEQ ID NO: 2 on the chromosome of the strain of the genus *Corynebacterium*, the initiation codon of the gene was replaced from ATG to TTG to attenuate the gene. Further, in order to construct a fragment therefor, primer 3 and primers 7 to 9 shown in Table 4 below were synthesized.

TABLE 4

| Gene | Primers used | Nucleotide sequences |
|---|---|---|
| SEQ ID NO: 2 | Primer 3 (SEQ ID NO: 5) | CCGCTCGAGACATCGAAATCGTA AGGGTA |
| | Primer 7 (SEQ ID NO: 9) | GATCCACAGTCCCAATATTCTCG CTTCTTC |
| | Primer 8 (SEQ ID NO: 10) | GAAGAAGCGAGAATATTGGGAC TGTGGATC |
| | Primer 9 (SEQ ID NO: 11) | CCGCTCGAGCAGCATTGACAAGC AGTTCT |

In order to amplify the ORF region (SEQ ID NO: 2) of the gene, primer 3 (SEQ ID NO: 5), primer 7 (SEQ ID NO: 9), primer 8 (SEQ ID NO: 10), and primer 9 (SEQ ID NO: 11) were synthesized so that an XhoI restriction enzyme site is present at both the 5' terminus and the 3' terminus. PCR was carried out with the chromosomal DNA of *Corynebacterium glutamicum* KCCM10741P as a template using primer 3, primer 7, primer 8, and primer 9. Herein, after denaturation at 95° C. for 5 minutes, PCR was carried out for a total of 30 cycles under the following conditions: denaturation at 94° C. for 30 seconds, annealing at 56° C. for 30 seconds, and polymerization at 72° C. for 1 minute. Thereafter, the polymerization reaction was carried out at 72° C. for 7 minutes. Next, a pDZ vector (Korean Patent No. 10-0924065), which is not replicable in *Corynebacterium glutamicum*, was treated with an XhoI restriction enzyme, and then the obtained PCR product was fusion-cloned. The fusion cloning was carried out using an In-Fusion® HD Cloning Kit (Clontech). Thereafter, the resultant was transformed into *E. coli* DH5α, and then plated on an LB solid medium containing kanamycin (25 mg/L).

A colony transformed with a plasmid having the desired gene inserted therein was selected by PCR, and then the plasmid was isolated using a plasmid extraction technique. The plasmid was named "pDZ-ΔRS2".

Example 8: Construction of *Corynebacterium glutamicum* KCCM10741P in which the Gene Comprising the Nucleotide Sequence of SEQ ID NO: 2 is Attenuated, and Evaluation of L-Arginine Productivity of the Constructed Strain The recombinant plasmid pDZ-ΔRS2 prepared in Example 7 was transformed into *Corynebacterium glutamicum* KCCM10741P, which is an L-arginine-producing strain, by homologous recombination on the chromosome (van der Rest et al., Appl Microbiol Biotechnol 52:541-545, 1999).

Next, the transformant was grown on a solid medium plate containing 4% sucrose to allow a second recombination to take place. The nucleotide sequence of the transformed *Corynebacterium glutamicum* strain obtained after the second recombination was analyzed using primer 3 and primer 9 to identify the strain in which the initiation codon of the gene comprising the nucleotide sequence of SEQ ID NO: 2 is substituted with TTG. The recombinant strain was named "*Corynebacterium glutamicum* KCCM10741P-R52".

Each of the parent strain *Corynebacterium glutamicum* KCCM10741P and the *Corynebacterium glutamicum* KCCM10741P-RS2 strain constructed above was cultured in the same manner as in Example 6 in order to analyze the L-arginine productivity. Thereafter, the amount of L-arginine produced was measured by HPLC, and the concentration of L-arginine analyzed is shown in Table 5 below.

TABLE 5

Analysis of L-arginine productivity of *Corynebacterium glutamicum* KCCM10741P in which the gene comprising the nucleotide sequence of SEQ ID NO: 2 is attenuated

| Strains | L-Arginine (g/L) | | | |
|---|---|---|---|---|
| | Batch 1 | Batch 2 | Batch 3 | Average |
| KCCM10741P | 4.2 | 4.2 | 4.1 | 4.17 |
| KCCM10741P-RS2 | 4.6 | 4.8 | 4.6 | 4.67 |

As shown in the results above, it was confirmed that when the gene comprising the nucleotide sequence of SEQ ID NO: 2 was attenuated in the L-arginine-producing strain KCCM10741P, the L-arginine productivity of the strain was increased by 12% on average.

Therefore, it was confirmed that the L-arginine productivity could be improved by attenuating the expression of the gene comprising the nucleotide sequence of SEQ ID NO: 2 in the microorganism of the genus *Corynebacterium*.

From the above results, it can be seen that in the strain in which the gene comprising the nucleotide sequence of SEQ ID NO: 2 is deleted or attenuated, the L-arginine productivity is increased, and this suggests that L-arginine can be mass-produced in the microorganism when the activity of the protein encoded by the gene is inactivated.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

Accession Number

Depositary Institution: Korean Culture Center of Microorganisms (KCCM) (International Depositary Authority)

Accession Number: KCCM12187P

Date of Deposit: Dec. 15, 2017

---

The invention claimed is:

1. A microorganism obtained from *Corynebacterium glutamicum* that produces L-arginine, wherein the microorganism is modified by inactivation of an endogenous protein comprising the amino acid sequence of SEQ ID NO: 1, and wherein the modified microorganism has increased production of L-arginine.

2. The microorganism of claim 1, wherein the protein is encoded by a gene consisting of a nucleotide sequence of SEQ ID NO: 2.

3. A method for producing L-arginine, comprising: culturing the microorganism of claim 1 in a medium.

4. The method for producing L-arginine of claim 3, further comprising:
recovering L-arginine from the microorganism or the medium.

5. A method for producing L-arginine, comprising: culturing the microorganism of claim 2 in a medium.

6. The method for producing L-arginine of claim 5, further comprising: recovering L-arginine from the microorganism or the medium.

* * * * *

SEQUENCE LISTING

<160> NUMBER OF SEQ ID NOS: 11

<210> SEQ ID NO 1
<211> LENGTH: 356
<212> TYPE: PRT
<213> ORGANISM: Corynebacterium glutamicum

<400> SEQUENCE: 1

```
Met Leu Leu Arg Ala Glu Glu Val Val Arg Gln Gly Gln Arg Gly Ile
1               5                   10                  15

Lys Leu His Val Glu Ala Gln His Glu His His His Arg His Leu
                20                  25                  30

Ser Thr Ile Lys Glu Leu Leu Val Asn Ala Asp Ile Pro Ala Gln Thr
            35                  40                  45

Lys Gln Asp Ala Leu Gly Val Phe Glu Leu Ile Ala Ile Ala Glu Gly
        50                  55                  60

Lys Val His Gly Ile Glu Pro Glu Lys Ile His Phe His Glu Val Gly
65                  70                  75                  80

Ala Trp Asp Ser Ile Ala Asp Ile Val Gly Val Cys Glu Ala Ile Arg
                85                  90                  95

Gln Leu Asn Pro Gly Leu Ile Ala Ala Ser Pro Ile Ala Leu Gly Phe
            100                 105                 110

Gly Arg Ile Lys Ala Ala His Gly Asp Ile Pro Val Pro Val Pro Ala
        115                 120                 125

Val Ala Glu Leu Val Lys Gly Trp Pro Thr Gln Thr Gly Ala Leu Met
    130                 135                 140

Glu Ser Thr Glu Pro Val Gly Glu Leu Ala Thr Pro Thr Gly Val Ala
145                 150                 155                 160

Leu Ile Arg His Phe Ala Thr Gln Asp Gly Pro Phe Pro Gly Gly Ile
                165                 170                 175

Ile Asn Glu Val Gly Ile Gly Ala Gly Thr Lys Asp Thr Ala Gly Arg
            180                 185                 190

Pro Asn Val Val Arg Ala Val Leu Phe Ser Thr Ser Gly Lys Ala Ala
        195                 200                 205

Ser Asn Pro Asp Thr Arg Thr Leu Val Gln Leu Glu Ala Asn Val Asp
    210                 215                 220

Asp Gln Asp Pro Arg Leu Trp Pro Gly Val Ile Glu Ser Leu Phe Ala
225                 230                 235                 240

Ala Gly Ala Val Ala Ala Trp Leu Thr Pro Ile Leu Met Lys Lys Gly
                245                 250                 255

Arg Pro Ala His Thr Val Ser Ala Leu Val Asp Ser Ser Glu Val Glu
            260                 265                 270

Ala Val Lys Thr Ala Leu Phe Ala Ala Thr Thr Thr Phe Gly Val Arg
        275                 280                 285

Ser Trp Glu Val Gln Arg Glu Gly Leu Asp Arg Arg Phe Glu Gln Val
    290                 295                 300
```

```
Glu Val Asp Gly Arg Thr Ile Asn Ile Lys Ile Gly Ser Arg Asn Gly
305                 310                 315                 320

His Asp Ile Ser Ala Gln Pro Glu Phe Glu Asp Ile Arg Ser Ala Ala
                325                 330                 335

Val Ala Leu Gly Ile Ser Glu Arg Glu Val Val Ala Arg Ile Pro Gln
            340                 345                 350

Gly Thr Thr Glu
        355

<210> SEQ ID NO 2
<211> LENGTH: 1071
<212> TYPE: DNA
<213> ORGANISM: Corynebacterium glutamicum

<400> SEQUENCE: 2
gtgcttttga gagcagaaga ggtagtgcgc caaggccaac gaggcatcaa actacatgta      60
gaagcacaac atgaacacca ccatcaccgc catttgagca ccattaaaga actgcttgtc     120
aatgctgaca tccctgcaca aaccaagcag gatgccttag gcgttttga actcatcgct      180 atcgctgaag aaaagtcca cggcatcgag ccggagaaaa tccacttcca tgaggtagga     240
gcttgggatt ccatcgcaga cattgtgggt gtgtgcgaag cgatcaggca gcttaaccca     300
ggtttgattg ctgcatctcc gattgcttta ggattcggac gcatcaaggc agctcacgga     360
gacattccag tgccagttcc agcagtggca gagctggtga aaggctggcc cacccaaacc     420
ggagctctta tggagagcac cgaacctgtt ggtgaattag ccaccccaac tggtgttgcg     480
ttgatccgtc actttgccac ccaagatggc cctttcccag gtggcatcat caatgaagtc     540
ggtatcggcg caggaactaa ggacaccgca gggcgtccca atgtggtgcg cgcggtcctg     600
ttcagcacct ccggtaaggc tgcctcaaac ccagacaccc gtaccctcgt gcaattggaa     660
gccaacgttg atgatcaaga cccacggctg tggccaggag taatagagag cctcttgcc      720 gctggcgcag tagctgcatg gctgactcca attttgatga agaagggccg tcctgcacat     780
acggtgtcag cattggtgga tagctccgag gtggaagcag tgaaaaccgc attatttgca     840
gccaccacga ctttgggg t cagatcatgg gaagtccagc gagaagggtt ggatcgtcgt     900
ttcgaacaag tcgaggtgga cggacgcacc atcaacatca agattggctc ccgaaatggc     960
cacgacatca gtgcacagcc cgagtttgaa gatattcggt ctgcagcggt ggccttggga    1020
atttcagaga gggaagttgt ggcaagaatt ccgcaaggca ccactgagta a             1071

<210> SEQ ID NO 3
<211> LENGTH: 25
<212> TYPE: DNA
<213> ORGANISM: Artificial Sequence
<220> FEATURE:
<223> OTHER INFORMATION: Primer 1

<400> SEQUENCE: 3
acctacaaca aagctctcat caacc                                            25

<210> SEQ ID NO 4
<211> LENGTH: 24
<212> TYPE: DNA
<213> ORGANISM: Artificial Sequence
<220> FEATURE:
<223> OTHER INFORMATION: Primer 2

<400> SEQUENCE: 4
```
ctaccctgtg aacacctac atct          24

<210> SEQ ID NO 5
<211> LENGTH: 29
<212> TYPE: DNA
<213> ORGANISM: Artificial Sequence
<220> FEATURE:
<223> OTHER INFORMATION: Primer 3

<400> SEQUENCE: 5
ccgctcgaga catcgaaatc gtaagggta          29

<210> SEQ ID NO 6
<211> LENGTH: 20
<212> TYPE: DNA
<213> ORGANISM: Artificial Sequence
<220> FEATURE:
<223> OTHER INFORMATION: Primer 4

<400> SEQUENCE: 6
cagcattgac aagcagttct          20

<210> SEQ ID NO 7
<211> LENGTH: 40
<212> TYPE: DNA
<213> ORGANISM: Artificial Sequence
<220> FEATURE:
<223> OTHER INFORMATION: Primer 5

<400> SEQUENCE: 7
agaactgctt gtcaatgctg ggccctttcc caggtggcat          40

<210> SEQ ID NO 8
<211> LENGTH: 29
<212> TYPE: DNA
<213> ORGANISM: Artificial Sequence
<220> FEATURE:
<223> OTHER INFORMATION: Primer 6

<400> SEQUENCE: 8
ccgctcgaga aggccaccgc tgcagaccg          29

<210> SEQ ID NO 9
<211> LENGTH: 30
<212> TYPE: DNA
<213> ORGANISM: Artificial Sequence
<220> FEATURE:
<223> OTHER INFORMATION: Primer 7

<400> SEQUENCE: 9
gatccacagt cccaatattc tcgcttcttc          30

<210> SEQ ID NO 10
<211> LENGTH: 30
<212> TYPE: DNA
<213> ORGANISM: Artificial Sequence
<220> FEATURE:
<223> OTHER INFORMATION: Primer 8

<400> SEQUENCE: 10
gaagaagcga gaatattggg actgtggatc          30

<210> SEQ ID NO 11
<211> LENGTH: 29
<212> TYPE: DNA
<213> ORGANISM: Artificial Sequence

```
<220> FEATURE:
<223> OTHER INFORMATION: Primer 9

<400> SEQUENCE: 11
ccgctcgagc agcattgaca agcagttct                                              29
```